US010752932B2

(12) United States Patent
Deligianni et al.

(10) Patent No.: US 10,752,932 B2
(45) Date of Patent: Aug. 25, 2020

(54) BIOSENSOR FOR MULTI-ANALYTE CHARACTERIZATION

(71) Applicant: INTERNATIONAL BUSINESS MACHINES CORPORATION, Armonk, NY (US)

(72) Inventors: Hariklia Deligianni, Alpine, NJ (US); Bruce B. Doris, Slingerlands, NY (US); Steven J. Holmes, Ossining, NY (US); Qinghuang Lin, Yorktown Heights, NY (US); Roy R. Yu, Poughkeepsie, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 60 days.

(21) Appl. No.: 15/671,938

(22) Filed: Aug. 8, 2017

(65) Prior Publication Data

US 2019/0048382 A1    Feb. 14, 2019

(51) Int. Cl.
*C12Q 1/00* (2006.01)
*G01N 27/327* (2006.01)
*G01N 33/94* (2006.01)

(52) U.S. Cl.
CPC ............. *C12Q 1/005* (2013.01); *C12Q 1/001* (2013.01); *C12Y 101/03004* (2013.01);
(Continued)

(58) Field of Classification Search
CPC ........... G01N 2600/00; G01N 33/5438; G01N 33/54346; B82Y 30/00
(Continued)

(56) References Cited

U.S. PATENT DOCUMENTS 6,063,637 A * 5/2000 Arnold ............... A61B 5/14539
422/82.01
8,883,645 B2 * 11/2014 Chang ................. H01L 29/4232
216/41
(Continued)

FOREIGN PATENT DOCUMENTS

JP         2004248714 A      9/2004
JP         2005293209 A      10/2005
(Continued)

OTHER PUBLICATIONS

Hasegawa et al., "Prediction of a Go/No-go Decision from Single-Trial Activities of Multiple Neurons in Monkey Superior Colliculus", Neurosci. Res. Inst., ICONIP 2007, Part II, LNCS 4985, pp. 997-1006, 2008.
(Continued)

*Primary Examiner* — Jonathan Han
(74) *Attorney, Agent, or Firm* — Cantor Colburn LLP; Vazken Alexanian

(57) ABSTRACT

Embodiments of the present invention are directed to a semiconductor device. A non-limiting example of the semiconductor device includes a semiconductor substrate. The semiconductor device also includes a plurality of metal nanopillars formed on the substrate. The semiconductor device also includes an amperometric sensor associated with one of the plurality of nanopillars, wherein the amperometric sensor is selective to an enzyme-active neurotransmitter. The semiconductor device also includes a resistivity sensor associated with a pair of nanopillars, wherein the resistivity sensor is selective to an analyte.

10 Claims, 19 Drawing Sheets

(52) U.S. Cl.
CPC .............. *C12Y 101/03017* (2013.01); *C12Y 104/03011* (2013.01); *C12Y 113/12004* (2013.01); *G01N 27/327* (2013.01); *G01N 33/9406* (2013.01); *G01N 33/9413* (2013.01); *G01N 2333/904* (2013.01); *G01N 2333/90241* (2013.01); *G01N 2333/90638* (2013.01)

(58) Field of Classification Search
USPC .......................... 204/400; 977/773, 742, 902
See application file for complete search history.

(56) References Cited

U.S. PATENT DOCUMENTS

| | | | | |
|---|---|---|---|---|
| 9,846,137 | B2* | 12/2017 | Bhansali | G01N 27/3278 |
| 2011/0024302 | A1* | 2/2011 | Li | C25D 13/04 |
| | | | | 205/183 |
| 2012/0118751 | A1* | 5/2012 | Cai | G01N 33/54346 |
| | | | | 205/122 |
| 2012/0263922 | A1* | 10/2012 | Advincula | C09D 5/1681 |
| | | | | 428/172 |
| 2012/0285833 | A1* | 11/2012 | Liu | G01N 33/5438 |
| | | | | 205/91 |

FOREIGN PATENT DOCUMENTS

| | | |
|---|---|---|
| JP | 2010274035 A | 12/2010 |
| JP | 2012053656 A | 3/2012 |
| JP | 2013178601 A | 9/2013 |
| JP | 2013202481 A | 10/2013 |

OTHER PUBLICATIONS

Hernandez et al., "Template Fabrication of Protein-Functionalized Gold-Polypyrrole—Gold Segmented Nanowires", Chem. Mater. 2004, 16, pp. 3431-3438.

Jeon et al., "Electrically Actuatable Smart Nanoporous Membrane for Pulsatile Drug Release", Nano Lett. 2011, 11, pp. 1284-1288.

Kan et al., "Imprinted electrochemical sensor for dopamine recognition and determination based on a carbon nanotube / polypyrrole film" Electrochimica Acta 63 (2012) pp. 69-75.

Kumpangpet et al., "Fabrication of Gold Nanoparticles / Polypyrrole / HRP Electrode for Phenol Biosensor by Electropolymerization", Engineering Journal, vol. 16, Issue 3; Accepted May 7, 2012; Published Jul. 1, 2012; Online at http://www.engj.org/; pp. 45-52.

Maouche et al., "Molecularly imprinted polypyrrole films: Some key parameters for electrochemical picomolar detection of dopamine", Journal of Electroanalytical Chemistry 685 (2012) pp. 21-27.

Mazzotta et al., "Electrosynthesis of molecularly imprinted polypyrrole for the antibiotic levofloxacin", Thin Solid Films 520 (2012) pp. 1938-1943.

Qin et al., "Microsensors for in vivo Measurement of Glutamate in Brain Tissue"; Sensors 2008, 8, DOI: 10.3390/s8116860; http://www.mdpi.com/journal/sensors; pp. 6860-6884.

Ryohei P. Hasegawa, et al., "Single trial-based prediction of a go/no-go decision in monkey superior colliculus", ScienceDirect, accepted May 8, 2006, Neural Networks 19 (2006) 1223-1232.

Schneider, Elizabeth "Oriented Attachment of Cytochrome P450 2C9 to a Self-Assembled Monolayer on a Gold Electrode as a Biosensor Design"; Electronic Theses and Dissertations UC Berkeley; Acceptance Date: Fall 2011; 108 pgs.

Schweiger et al., "Electropolymerized Molecularly Imprinted Polypyrrole Film for Sensing of Clofibric Acid" Sensors 2015, 15, doi: 10.3390/s150304870; www.mdpi.com/journal/sensors; ISSN 1424-8220; pp. 4870-4889.

Sharma et al., "Molecular imprinted nanoPolymer nanomaterials: application in biomolecule recognition", NSTI-Nanotech 2010, www.nsti.org; ISBM 978-1-4398-3415-2; vol. 3, 2010; pp. 270-273.

Tsai et al., "Modification of platinum microelectrode with molecularly imprinted over-oxidized polypyrrole for dopamine measurement in rat striatum"; Sensors and Actuators B 171-172 (2012) pp. 93-101.

Deligianni et al., "Biosensor for Multi-Analyte Characterization," U.S. Appl. No. 16/691,737, filed Nov. 22 2019.

List of IBM Patents or Patent Applications Treated as Related; Date Filed: Nov. 22 2019, 2 pages.

Yan, et al., "Characteristic and Synthetic Approach of Molecularly Imprinted Polymer," Int. J. Mol. Sci. 2006, 7, 155-178; (24 pages).

* cited by examiner

BIOSENSOR FOR MULTI-ANALYTE CHARACTERIZATION

BACKGROUND

The present invention generally relates to fabrication methods and resulting structures for biosensors. More specifically, the present invention relates to biosensors for multi-analyte characterization.

Biosensors can be useful for the detection and characterization of biomolecules. There exist a variety of different types of bio sensors, including calorimetric biosensors, potentiometric biosensors, acoustic wave biosensors, amperometric biosensors, and optical biosensors. Biosensors can be tailored to sense a specific analyte for specific applications. For instance, specific neurotransmitters, such as dopamine, can be detected in vivo for the study of neurological disorders.

Many biological processes, disorders, and diseases simultaneously implicate actions and interactions of a plurality of biomolecules. Studies of the interplay and relationships between such molecules can require sensing of multiple analytes. Moreover, the location of such biomolecules can be an important factor in biological function. For example, in the case of neurotransmitters, neurotransmitters can travel across a short distance of a synapse and the locations of such neurotransmitters can play an important role in understanding neurological processes. In addition, a neuron can have a length of from about 10 to 100 microns and, depending on biological state, different biomolecules can be present at different locations along the neurotransmitter. In such applications, multi-analyte sensing capability and biosensors with nanoscale resolution can provide valuable information.

SUMMARY

Embodiments of the present invention are directed to a method for fabricating a semiconductor device. A non-limiting example of the method includes forming a plurality of nanopillars on a substrate, the plurality of nanopillars including a first nanopillar and a pair of adjacent nanopillars. The method also includes forming an insulating layer on the plurality of nanopillars to generate a plurality of lined nanopillars. The method also includes removing the insulating layers from upper portions of the pair of adjacent nanopillars to generate exposed adjacent nanopillar portions. The method also includes forming a resistivity sensor on the exposed adjacent nanopillar portions. The method also includes removing the insulating layer from the first nanopillar to generate an exposed first nanopillar portion. The method also includes forming an amperometric sensor on the exposed first nanopillar portion. Such embodiments of the invention can advantageously form a semiconductor device with multi-analyte sensing capability that can provide nanoscale resolution.

Embodiments of the present invention are directed to a semiconductor device. A non-limiting example of the semiconductor device includes a semiconductor substrate. The semiconductor device also includes a plurality of metal nanopillars formed on the substrate. The semiconductor device also includes an amperometric sensor associated with one of the plurality of nanopillars, wherein the amperometric sensor is selective to an enzyme-active neurotransmitter. The semiconductor device also includes a resistivity sensor associated with a pair of nanopillars, wherein the resistivity sensor is selective to an analyte. Such embodiments of the invention can advantageously sense multiple biological analytes simultaneously and in real-time.

Embodiments of the present invention are directed to a multi-analyte biosensor. A non-limiting example of the biosensor includes a substrate. The biosensor also includes a first nanopillar including a base connected to the substrate. The biosensor also includes a second nanopillar including a base connected to the substrate, wherein the second nanopillar is adjacent to the first nanopillar. The biosensor also includes an imprinted polymer physically contacting at least a portion of the first nanopillar and at least a portion of the second nanopillar, wherein the imprinted polymer includes a conductive porous polymer including a plurality of cavities with affinity to a first analyte. The biosensor also includes a third nanopillar including a base connected to the substrate, wherein the third nanopillar is lined with an amperometric sensor polymer including a plurality of binding sites with affinity to a second analyte. Such embodiments can advantageously detect both enzymatic and non-enzymatic biological analytes in a biological tissue sample.

Embodiments of the present invention are directed to a multi-analyte biosensor. A non-limiting example of the biosensor includes a semiconductor substrate. The multi-analyte biosensor also includes a first sensing region including a first plurality of nanopillars connected to a first conductive polymer selective to a first biomolecule, wherein the first sensing region is connected to the semiconductor substrate. The multi-analyte biosensor also includes a second sensing region including a second plurality of nanopillars connected to a second conductive polymer selective to a second biomolecule, wherein the second sensing region is connected to the semiconductor substrate and wherein the second biomolecule is different than the first biomolecule. The multi-analyte biosensor also includes an interface layer connecting the semiconductor substrate to a processor. The multi-analyte biosensor also includes a communications interface. Such embodiments can advantageously sense multiple analytes and their positional information in real time and provide concentration and position information to a user.

Embodiments of the invention are directed to a computer-implemented method of multi-analyte detection. A non-limiting example of the method includes receiving, to a processor, a signal from a multi-analyte sensor in contact with a biological tissue, wherein the multi-analyte sensor includes a resistivity sensor and an amperometric sensor. The method also includes determining, by the processor, a resistivity value from the resistivity sensor. The method also includes generating, by the processor, a concentration of a first analyte based at least in part upon the resistivity value. The method also includes determining, by the processor, an electrical current from the amperometric sensor. The method also includes generating, by the processor, a concentration of a second analyte based at least in part upon the electrical current. Such embodiments can advantageously determine the concentration of multiple analytes at nanoscale resolution.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

The specifics of the exclusive rights described herein are particularly pointed out and distinctly claimed in the claims at the conclusion of the specification. The foregoing and other features and advantages of the embodiments of the invention are apparent from the following detailed description taken in conjunction with the accompanying drawings in which:

FIGS. 2A-2B depicts another exemplary biosensor according to embodiments of the invention, in which:

FIG. 2A depicts a cross-sectional side view of the exemplary biosensor, and

FIG. 2B depicts a top down view of the exemplary biosensor.

FIGS. 3A-3L depict an exemplary biosensor after various fabrication operations according to embodiments of the invention, in which:

FIG. 3A illustrates the exemplary biosensor after a fabrication operation according to embodiments of the invention;

FIG. 3B illustrates the exemplary biosensor after a fabrication operation according to embodiments of the invention;

FIG. 3C illustrates the exemplary biosensor after a fabrication operation according to embodiments of the invention;

FIG. 3D illustrates the exemplary biosensor after a fabrication operation according to embodiments of the invention;

FIG. 3E illustrates the exemplary biosensor after a fabrication operation according to embodiments of the invention;

FIG. 3F illustrates the exemplary biosensor after a fabrication operation according to embodiments of the invention;

FIG. 3G illustrates the exemplary biosensor after a fabrication operation according to embodiments of the invention;

FIG. 3H illustrates the exemplary biosensor after a fabrication operation according to embodiments of the invention;

FIG. 3I illustrates the exemplary biosensor after a fabrication operation according to embodiments of the invention;

FIG. 3J illustrates the exemplary biosensor after a fabrication operation according to embodiments of the invention;

FIG. 3K illustrates the exemplary biosensor after a fabrication operation according to embodiments of the invention;

FIG. 3L illustrates the exemplary biosensor after a fabrication operation according to embodiments of the invention;

Figure 1:
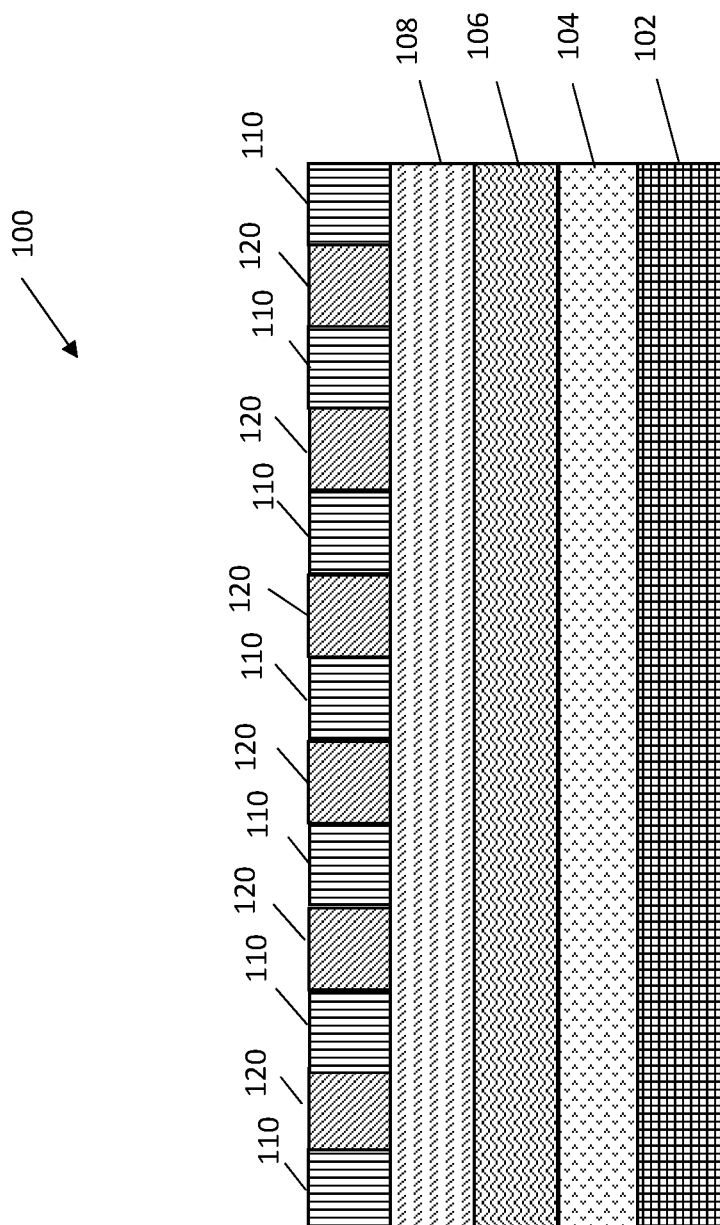
FIG. 1 depicts an exemplary biosensor according to embodiments of the invention.

The diagrams depicted herein are illustrative. There can be many variations to the diagram or the operations described therein without departing from the spirit of the invention. For instance, the actions can be performed in a differing order or actions can be added, deleted or modified. Also, the term "coupled" and variations thereof describes having a communications path between two elements and does not imply a direct connection between the elements with no intervening elements/connections between them. All of these variations are considered a part of the specification.

In the accompanying figures and following detailed description of the described embodiments, the various elements illustrated in the figures are provided with two or three digit reference numbers. With minor exceptions, the leftmost digit(s) of each reference number correspond to the figure in which its element is first illustrated.

DETAILED DESCRIPTION

For the sake of brevity, conventional techniques related to semiconductor device and integrated circuit (IC) fabrication may or may not be described in detail herein. Moreover, the various tasks and process steps described herein can be incorporated into a more comprehensive procedure or process having additional steps or functionality not described in detail herein. In particular, various steps in the manufacture of semiconductor devices and semiconductor-based ICs are well known and so, in the interest of brevity, many conventional steps will only be mentioned briefly herein or will be omitted entirely without providing the well-known process details.

Turning now to an overview of technologies that are more specifically relevant to aspects of the invention, biosensors can play an important role in the characterization of a variety of different biomolecules. In neuroscience applications, for example, bio sensors of different types can be used to detect neurotransmitter function or to assess and investigate abnormalities.

Several neurodegenerative diseases are associated with abnormal neurotransmitter function. For example, Parkinson's disease can result from a loss of dopamine secreting cells, and a resultant decrease of dopamine, in the substantia nigra area of the brain. Another neurotransmitter, glutamate (or glutamic acid), is associated with and can play a key role in a number of neurological disorders, including ischemia, schizophrenia, epilepsy, Alzheimer's disease (AD), and Parkinson's disease (PD). Abnormal levels of neurotransmitters, or accumulation of neurotransmitters in particular regions, can signal abnormal function. Glutamate and other neurotransmitters, such as dopamine, can send signals in the brain and throughout the body. In the case of brain injury or neurological disorders, for instance, glutamate can accumulate outside of cells due to errors in glutamate transport or impaired glutamate uptake.

Thus, neurotransmitter identity and location can provide important information for the identification and characterization of a variety of conditions. In addition, such information can provide valuable information for treatment of neurological disorders and illnesses because, for example, some of the primary medications used to treat such conditions seek to change the effects of one or more transmitters, such as dopamine.

Sensing of particular neurotransmitters can be accomplished in a variety of ways, depending on the molecule and associated properties in question. Biosensors can be categorized by type, for example, such as calorimetric biosensors, potentiometric biosensors, acoustic wave biosensors, resistivity biosensors, amperometric biosensors, and optical biosensors.

The use and selection of biosensor type can depend, for example, upon the method of metabolism of the neurotransmitter of interest. Enzymatically controlled neurotransmitter metabolism can in some cases be investigated by enzyme-based amperometric sensors. Enzyme-based amperometric sensors can include an enzyme with specificity toward a desired analyte embedded in a polymer on an electrode. Such sensors can be formed, for example, by electropolymerization of the enzyme and substrate around an electrode, such as a metal electrode. After polymerization and prior to use, the substrate can be removed from the sensor providing an available binding site for substrate detection in vivo.

Such amperometric sensors are known and can rely, for example, upon electron generation through enzymatic oxidation of the analyte on the electrode, which can result in measurable current. Glutamate metabolism, for example, is enzymatically controlled and can have an electrical current in decomposition, through the release of electrons that are in proportion to its concentration. Related measurements can be accomplished, for example by embedding glutamate oxidase enzyme in a conformal polymer grown on a metal electrode. In such implementations, electrical current can be used to determine concentration of enzymatically metabolized analytes.

Non-enzymatically controlled neurotransmitters can be measured with resistivity-based methods. Dopamine metabolism, for instance, can be measured without enzymatic binding. Dopamine and other non-enzymatically controlled neurotransmitters can be detected and measured, for example, by taking resistivity measurements from an organic electrode imprinted with the target neurotransmitter. By electropolymerizing a polymeric substrate with the desired analyte, and then removing the analyte from the imprinted substrate, a receptor cavity complimentary to the analyte can be generated in a molecularly imprinted polymer (MIP). Such resistivity sensors are known and can rely upon, for example, resistance changes in an unbound versus an analyte-bound sensor. The measured resistivity in such implementations can be proportional to the concentration of the target analyte.

Conventional biosensors that can detect or measure a single neurotransmitter provide only a limited view of neurological processes and conditions. For example, a plurality of neurotransmitters can each play a distinct and simultaneous role in neurological impairments. Measurement of multiple neurotransmitters can require the use of multiple sensing systems, which can be cumbersome, cost-prohibitive, and could preclude time-sensitive or time-dependent measurements of multiple analytes or measurement of multiple analytes in the same region.

In addition, although some neurotransmitter activity occurs on the micron and sub-micron scale, conventional biosensors can lack precision needed to measure activity at that scale. Conventional biosensors that can only measure on the scale of five to ten microns, for example, cannot detect or sense neurotransmitters across the surface of a single neuron, which measurements call for nanometer scale resolution.

Aspects of the invention address the above-described shortcomings of the prior art by providing a single device that can simultaneously measure multiple biomolecules in the same region. In some embodiments, multiple types of biosensors are included in a single device. Embodiments of the invention include biosensors capable of nanoscale resolution for sensing neurotransmitters. Embodiments of the invention can include a large array of nanopillars, wherein each nanopillar can be selectively wired to allow distinct measurement from each pillar. Each pillar can be formed or treated such that it is selective to a single neurotransmitter. Embodiments of the invention include a plurality of nanopillars formed of a conductive metal, such as gold or platinum, wherein each nanopillar can be selectively coated with an organic polymer that is sensitive to a particular target molecule. In some embodiments of the invention, horizontal organic electrodes associated with one or more nanopillars can, by measuring resistivity, detect and/or characterize specific biomolecules. In some embodiments of the invention, a sensor includes one or more sensors, such as horizontal organic electrodes, for non-enzymatic neurotransmitter detection and/or characterization and one or more sensors for enzymatic neurotransmitter detection and/or characterization. In some embodiments of the invention, electrically functional nano-pillar electrodes are created across a portion of a device substrate including structures of conductive polymer between two or more electrodes. The conductive polymer can include embedded molecular recognition sites. In some embodiments of the invention a biosensor for multi-analyte detection is implanted into a neural tissue region. Embodiments of the invention can provide biomolecule concentration over time and for a specific biomolecule type.

Turning now to a more detailed description of aspects of the present invention, FIG. 1 depicts an exemplary structure 100 for multi-analyte characterization according to embodiments of the invention. The exemplary structure 100 can include a first sensing region 110 and a second sensing region 120. The first sensing region 110 and second sensing region 120 can include biosensors for detecting different analytes. For example, in an exemplary embodiment of the invention, a first sensing region 110 detects and measures a first neurotransmitter, such as dopamine, and a second sensing 120 region detects and measures a second neurotransmitter, such as glutamate. The sensing regions 110, 120 can be connected to a processor 106 through an interface layer 108. The processor is in connection with an energy supply layer 104, such as a layer including a battery or capacitor, and a communications interface 102, such as a graphical user interface.

Although FIG. 1 depicts two sensing regions, it is understood that the number of sensing regions is not limited to two and can vary depending upon the number and types of analytes to be measured. For example, some embodiments of the invention can include tens or hundreds of sensing regions.

Neurotransmitters and other analytes that can be detected or measured according to embodiment of the invention include any analyte suitable for the detection methods herein.

Analytes that can be detected with resistivity sensors can include analytes that can be imprinted into a polymer matrix with suitable selectivity and that can experience a change in resistivity upon analyte binding. Such analytes can include, but are not limited to, dopamine, epinephrine, ascorbic acid, and uric acid.

Analytes that can be detected with amperometric sensors can include analytes that have associated enzymes that are amenable to matrix immobilization without a loss in functionality and that can effect a change in current, for instance through oxidization of the analyte. For example, suitable enzymes for amperometric sensors can include, but are not limited to, glutamate oxidase, lactate oxidase, glucose oxidase, and choline oxidase. Enzymes for amperometric sensors can be selected based upon the desired analyte. Exemplary analytes that can be sensed with amperometric sensors can include, but are not limited to, glutamate, lactate, glucose, choline, adenosine, and gamma-amino-butyric acid (GABA).

Biosensors according to embodiments of the invention can include amperometric sensors and/or resistivity sensors. In some embodiments of the invention, the structure includes a plurality of amperometric sensors. In some embodiments of the invention, the structure includes a plurality of resistivity sensors. In some embodiments of the invention, the structure includes both amperometric and resistivity sensors.

In some embodiments of the invention a structure includes a plurality of amperometric sensors, wherein each of the plurality of amperometric sensors detects the same analyte. In some embodiments of the invention, a system includes different types of amperometric sensors, in which different sensors are capable of sensing distinct analytes. In some embodiments of the invention a structure includes a plurality of amperometric sensors that detect two or more different analytes.

In some embodiments of the invention a structure includes a plurality of resistivity sensors, wherein each of the plurality of resistivity sensors detects the same analyte. In some embodiments of the invention, a system includes different types of resistivity sensors, in which different sensors are capable of sensing distinct analytes. In some embodiments of the invention a structure includes a plurality of resistivity sensors that detect two or more different analytes.

Figure 2A:
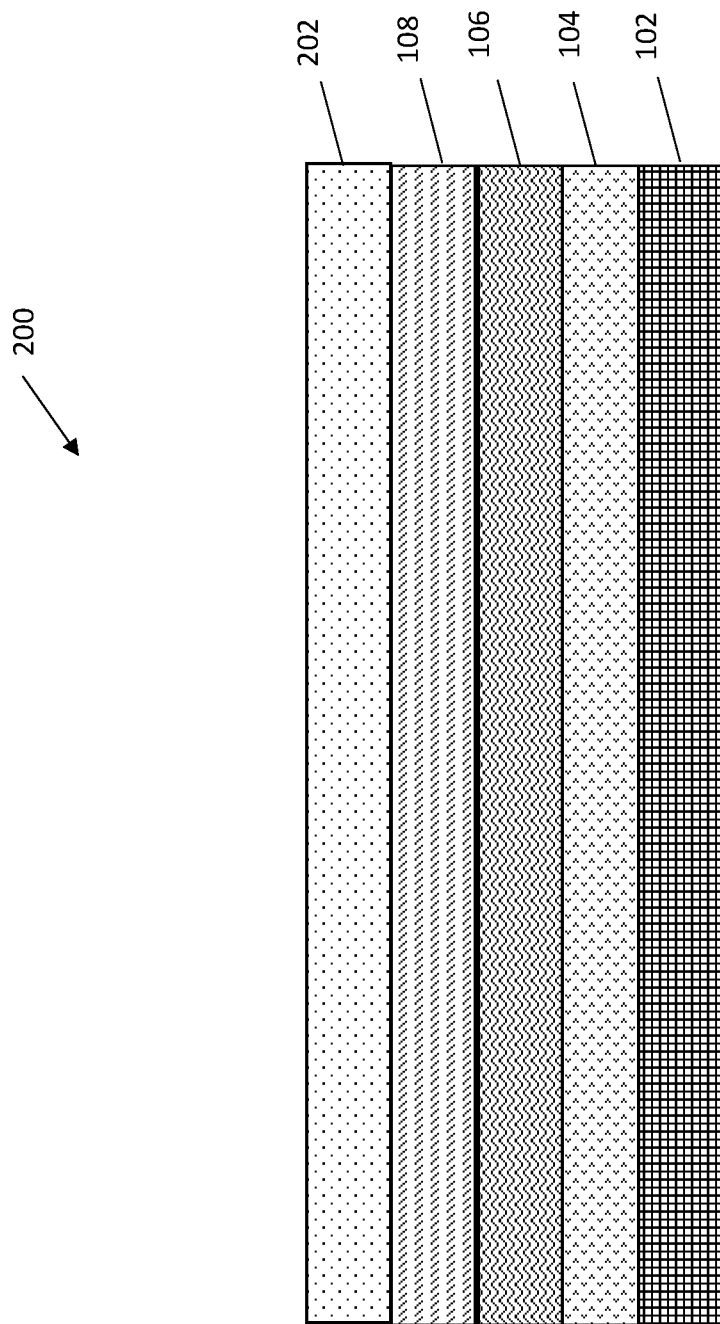
Figure 2B:
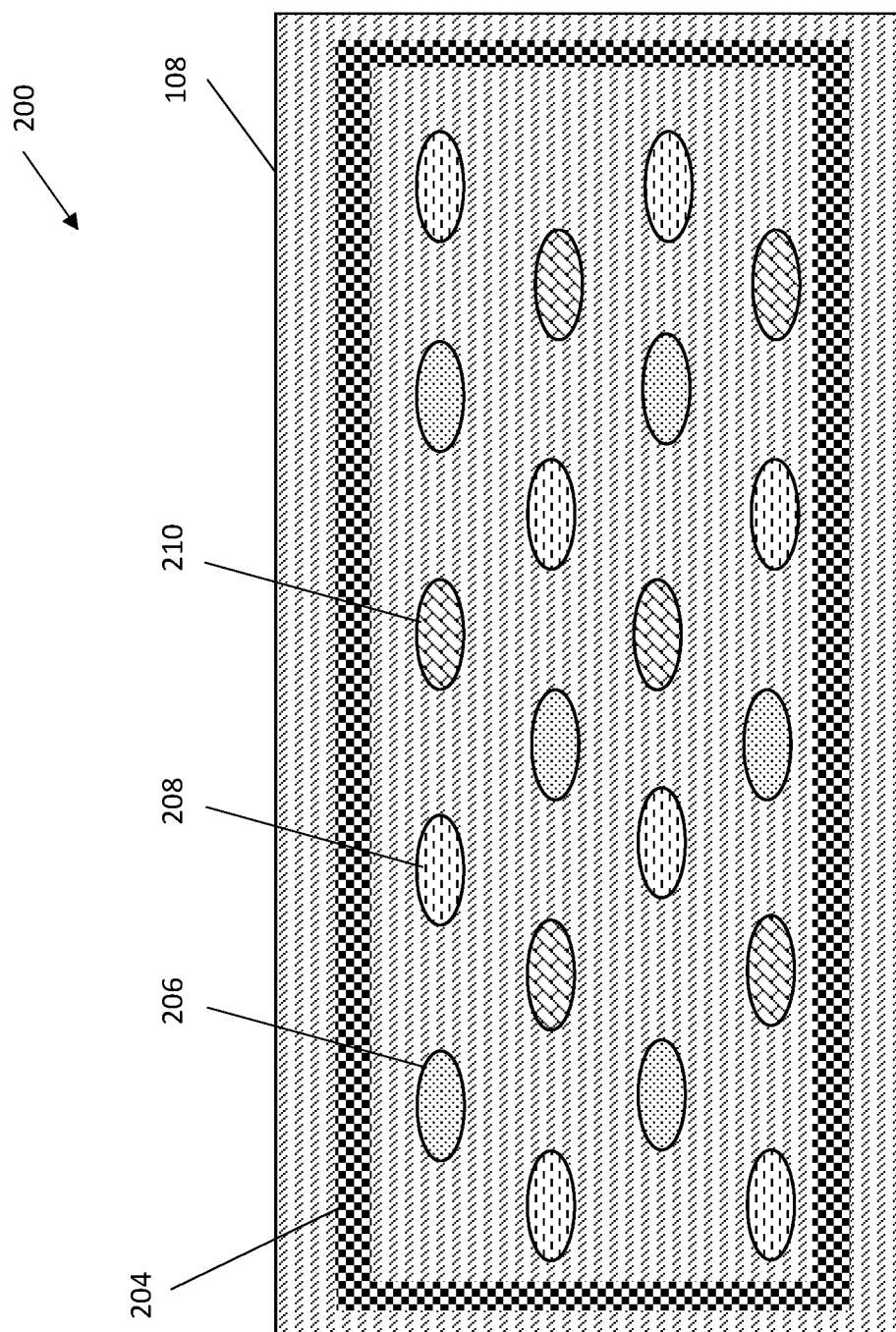

FIGS. 2A and 2B depict another exemplary structure 200 for multi-analyte characterization according to one or more embodiments of the present invention in which FIG. 2A is a cross-sectional side view of the structure 200 and FIG. 2B is a top-down view of the structure of FIG. 2A. The structure 200 can include a sensing layer 202. The sensing layer 202 can include multiple types of chemical sensors 206, 208, 210, dispersed upon an interface layer 108. The chemical sensors 206, 208, 210 can be in any pattern and any number and can be tailored to the desired application. In some embodiments of the invention, the sensing layer can include more than two different types of chemical sensors. For example, in some embodiments of the invention, the sensing layer can include three different types of sensors (as shown in FIG. 2B) or, for example, twenty different types of sensors (not shown). The chemical sensors 206, 208, 210 can be formed upon one or more nanopillars and can include a single nanopillar structure or multiple nanopillar structures (not shown in FIGS. 2A and 2B). The chemical sensors can be spaced at a distance tailored to the desired application. In some embodiments of the invention, the chemical sensors 206, 208, 210 are spaced apart from one another at a distance of about 200 nanometers (nm) to about 2 microns.

As is shown in FIG. 2B, the structure 200 can include a microfluidic structure 204 surrounding the chemical sensors 206, 208, 210. In some embodiments of the invention, the microfluidic structure 204 is in contact with some or all of the chemical sensors. The structure 200 can also include a processor 106 in communication with the sensing region 202 through an interface layer 108. The processor is in connection with an energy supply layer 104, such as a layer including a battery or capacitor, and a communications interface 102, such as a graphical user interface.

FIGS. 3A-3L depict an exemplary method of fabricating a sensor according to one or more embodiments of the present invention.

Figure 3B:
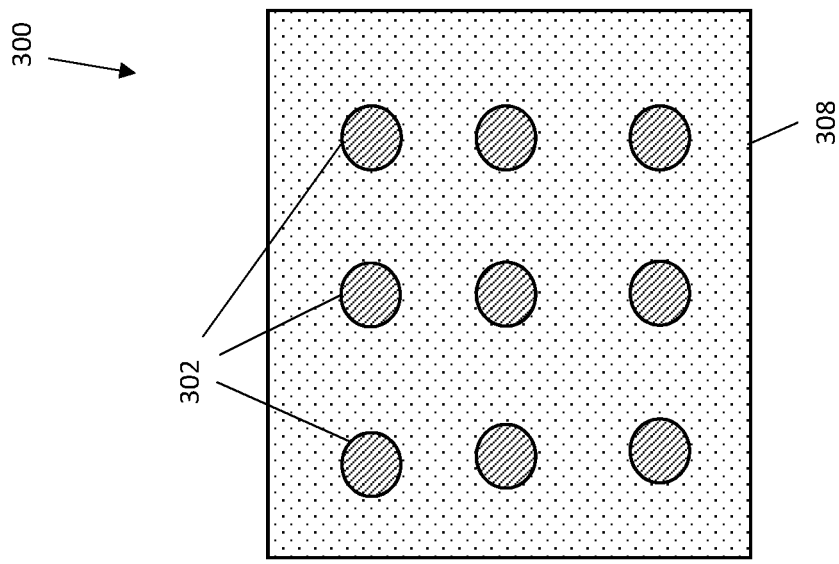
Figure 3A:
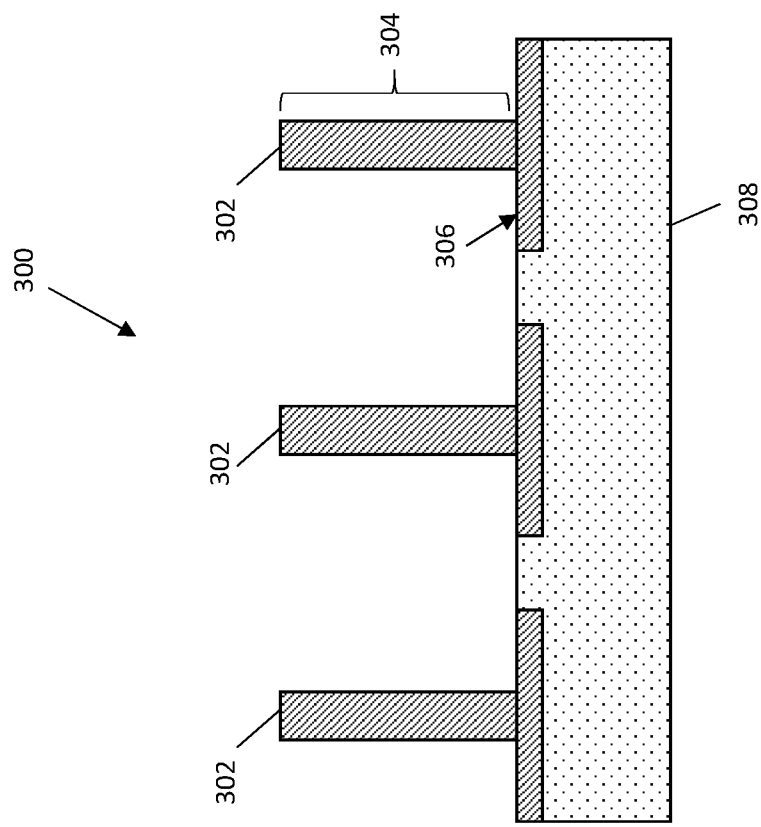

FIG. 3A depicts a cross sectional side view of an exemplary structure 300 after formation of a substrate 308 including a plurality of nanopillars 302. The nanopillars 302 can each have a base 306 and a pillar portion 304. The nanopillars 302 can be formed on the substrate by depositing a resist layer, such as an organic planarization layer (OPL) (not shown in FIG. 3A) on the substrate 308, patterning holes in the resist layer with known lithography techniques, and plating metal onto the structure 300 in the holes in the resist layer. After plating the metal of the nanopillars 302, the resist layer can be removed from the structure. It is understood that although the exemplary structure depicts three rows of nanopillars 302, the number of nanopillars can vary and can be tailored to the desired application. For example, in some embodiments of the invention a structure can include tens or hundreds of rows of nanopillars 302.

In some embodiments of the invention, the nanopillars are spaced apart at a pitch of about 200 nm to about 600 nm, such as about 200 nm to about 500 nm, or about 200 nm to about 400 nm, or about 200 nm to about 300 nm. In some embodiments of the invention, the nanopillars can have a height of about 100 nm to about 1000 nm, such as about 500 nm to about 800 nm. In some embodiments of the invention, the nanopillars can have a diameter of about 50 nm to about 100 nm.

FIG. 3B depicts a top down view of the exemplary structure 300 depicted in FIG. 3A showing an exemplary ordered arrangement of nanopillars 302 formed on a substrate 308. In other embodiments of the invention, not shown in FIG. 3B, unordered or irregularly spaced nanopillars 302 can be formed on a substrate.

Nanopillars 302 can be formed of conductive metal, such as platinum, gold, silver, nickel, palladium, tin, or copper. In some embodiments of the invention, nanopillars 302 include platinum. In some embodiments of the invention, nanopillars include copper.

The substrate 308 can include known semiconductor materials, such as silicon (e.g., such as a silicon wafer), silicon germanium, or other suitable rigid supporting material. Associated wiring (not shown in FIG. 3A) can be fabricated using known processes, such as convention back end of the line technologies.

Figure 3C:
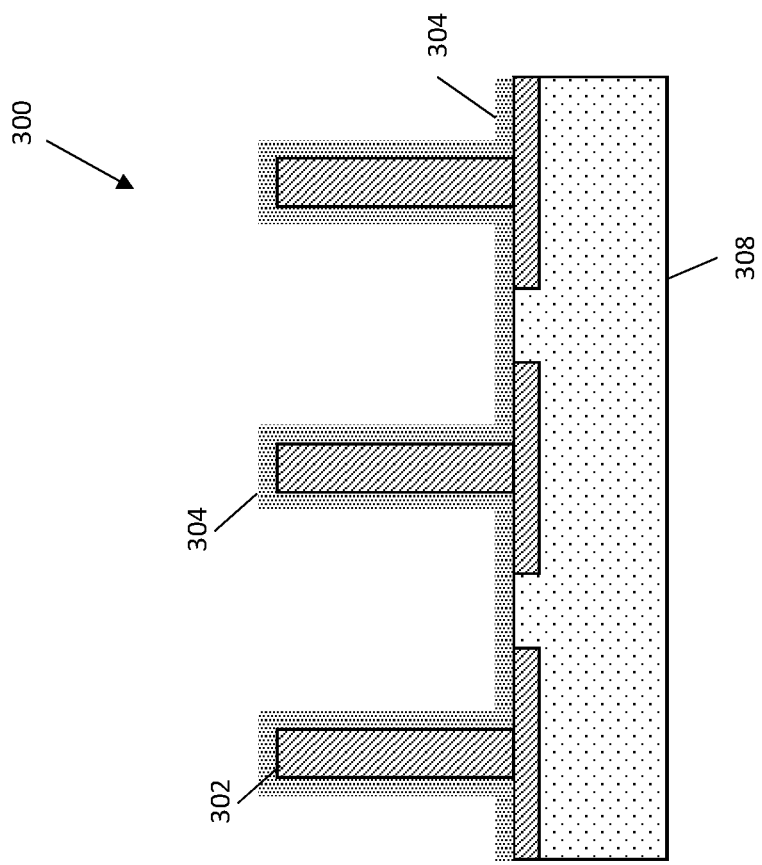

In some embodiments of the invention, after forming the nanopillars 302, the nanopillars can be lined with an insulating layer 304, as is depicted in FIG. 3C. The insulating layer can include any known insulating material suitable for semiconductor applications, such as aluminum oxide, silicon oxide, or a composite of oxides. The insulating layer 304 can be deposited on the structure 300, for instance, by atomic layer deposition (ALD) using known techniques.

Figure 3D:
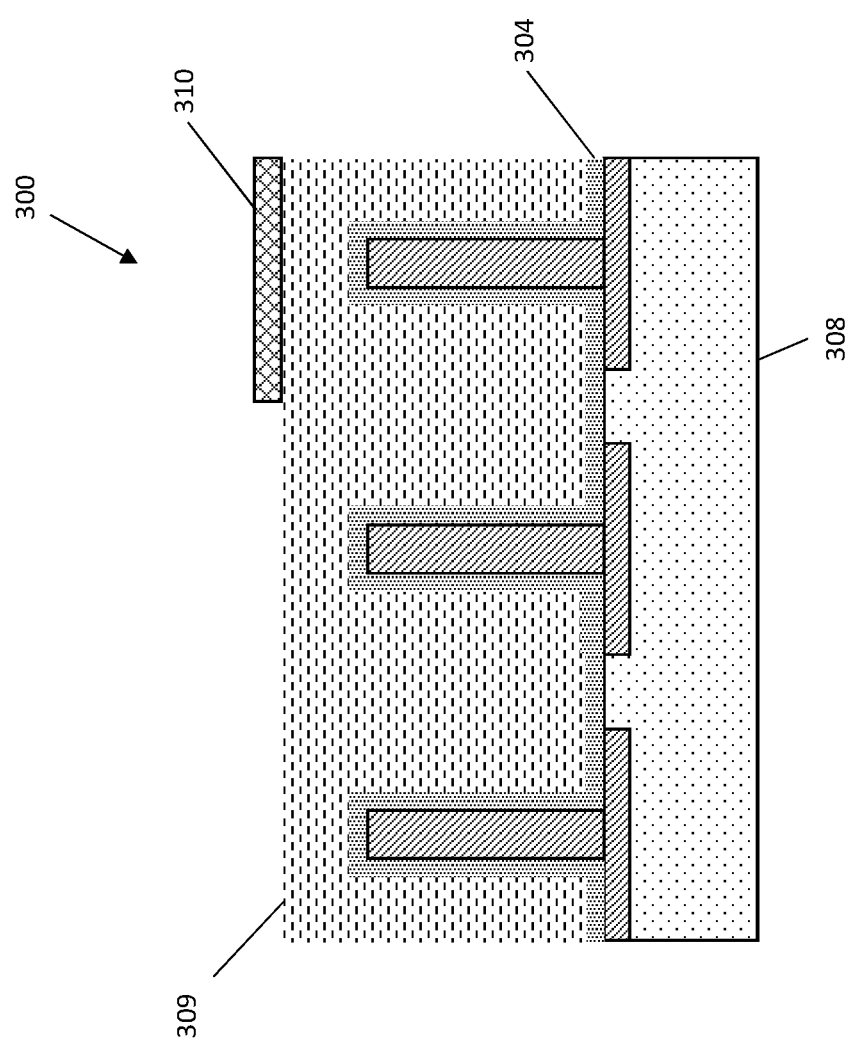

In some embodiments of the invention, after lining the nanopillars with an insulating layer 304, one or more resistivity sensors can be formed on the structure. A resistivity sensor can be fabricated by depositing an OPL layer 309 on the structure 300 and patterning a hard mask layer 310 on the OPL layer 309, as is depicted in FIG. 3D. The OPL layer 309 can include, for instance, an organic spin-on material. The hardmask layer 310 can be patterned such to expose one or more nanopillars, such as two nanopillars, which can function as part of a resistive sensor. The hardmask layer 310 can include, for example, titanium and can have a thickness of about 20 nanometers.

Figure 3E:
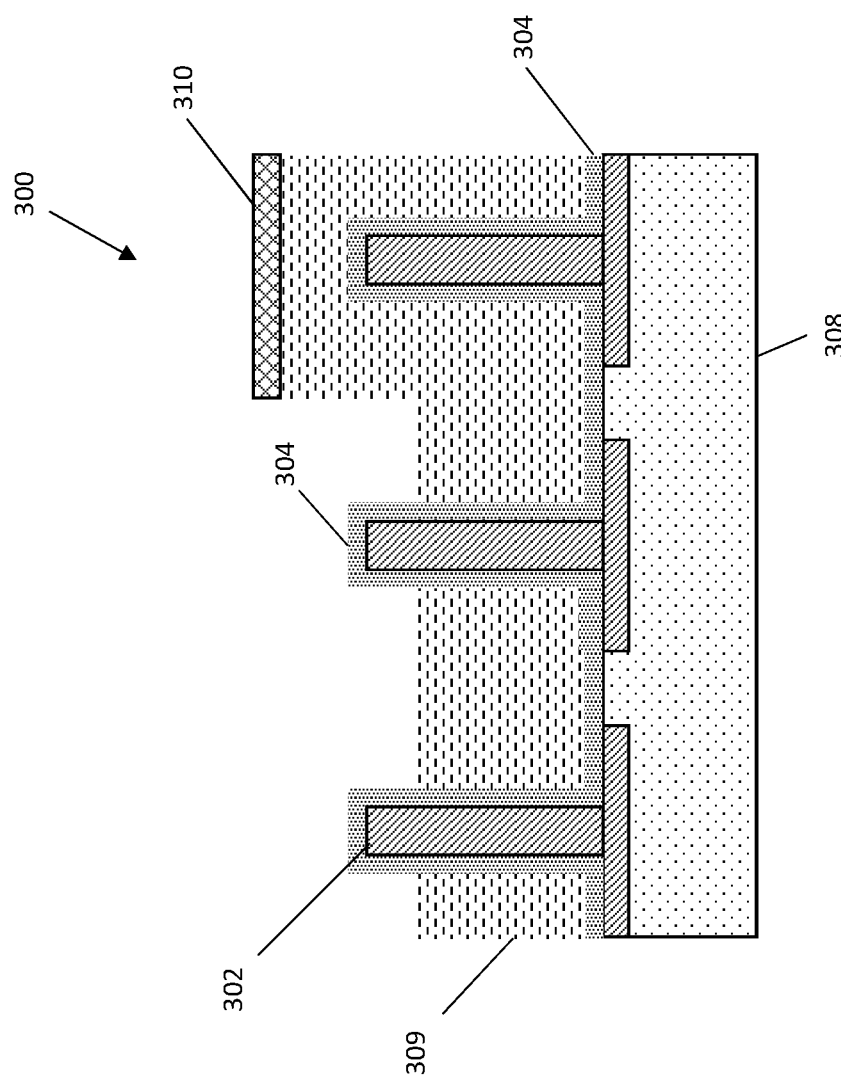

After patterning the hardmask layer 310, the unmasked OPL layer 308 can be etched to expose a portion of insulating layer 304 on one or more electrodes 302, as is illustrated in FIG. 3E. In some embodiments of the invention, not shown in FIG. 3E, the unmasked OPL layer 309 can be etched to expose all of the insulating layer 304 on one or more electrodes. Etching the OPL layer 309 can include, for instance, reactive ion etch (RIE). The resulting structure 300 can include one or more recessed areas for depositing polymeric material.

Figure 3F:
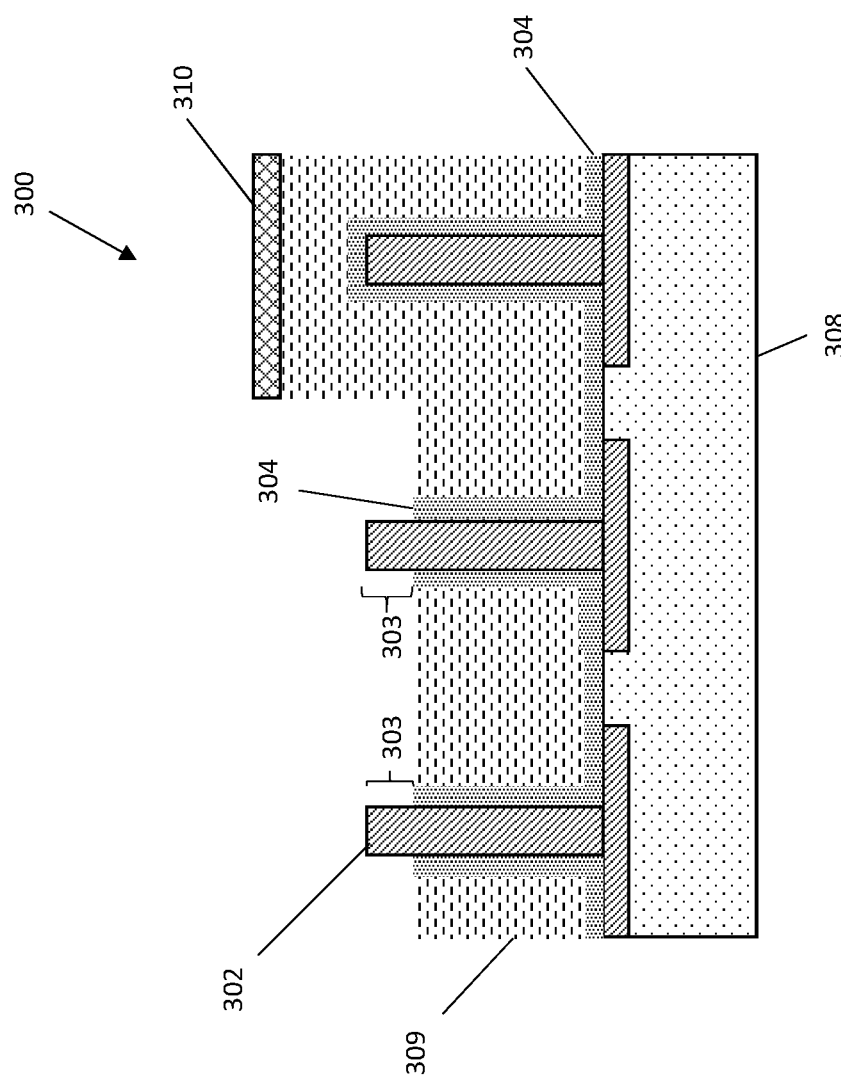

After recessing the OPL layer 309, the structure can be wet etched, for instance with dilute HF (DHF), to remove the portion of the insulating layer 304 on the electrodes previously exposed through etching the OPL layer 309, as is illustrated in FIG. 3F. In some embodiments of the invention, upper portions 303 of a pair of adjacent electrodes 302 are exposed through etching with DHF, as is shown. In some embodiments of the invention, more than an upper portion of the electrodes 302, for example, half of the vertical height or all of the vertical height, is exposed through etching with DHF (not shown in FIG. 3F).

Figure 3G:
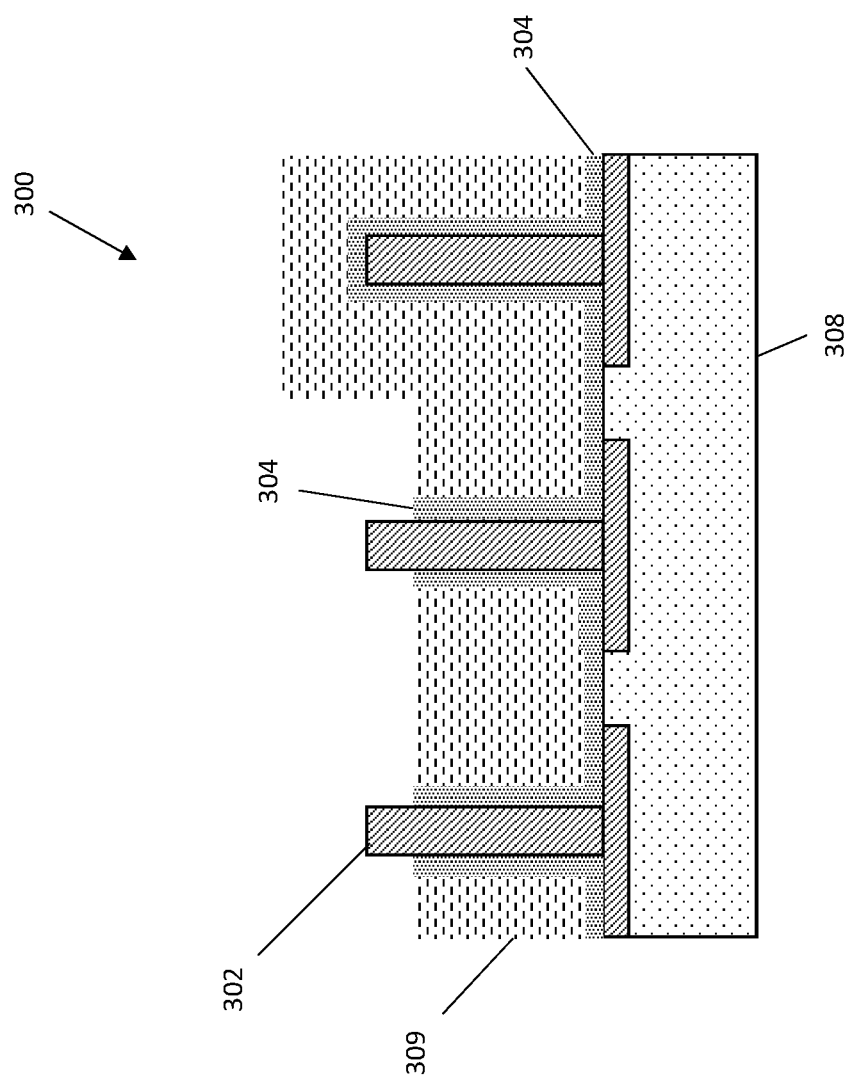

The hard mask layer 310 can be removed from the structure 300 by wet etching, for instance by wet etching with hydrogen peroxide. FIG. 3G illustrates an exemplary structure 300 after removal of the hard mask layer 310.

Figure 3H:
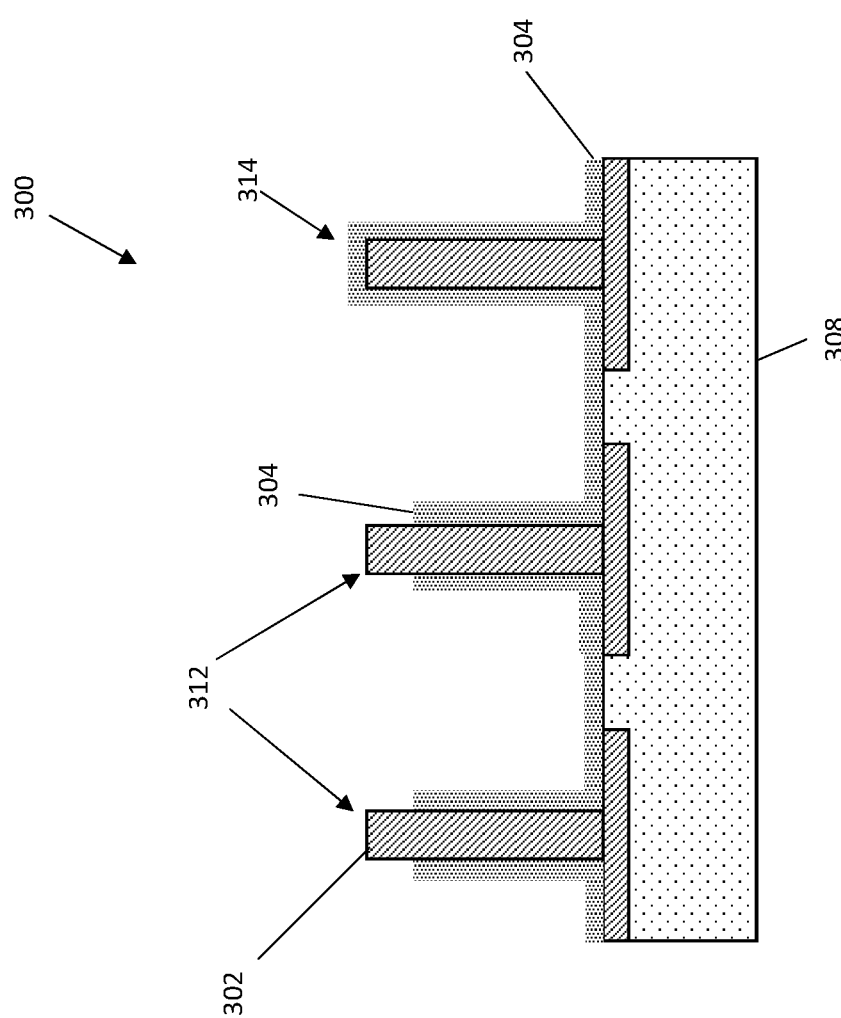

After removing the hard mask layer 310, remaining OPL layer 309 can be removed from the structure 308. For example, OPL layer 309 can be stripped from the structure 300 with plasma treatment, such as $O_2$ plasma or $N_2/H_2$ plasma etching. FIG. 3H depicts an exemplary structure after removal of the OPL layer 309. As can be seen in FIG. 3H, a resultant structure 300 can include adjacent electrodes 312 that are partially exposed and partially coated with insulating layer 304 and one or more fully insulated electrodes 314. Partially exposed electrodes 312 can serve as substrates for electro-polymerized material to form resistivity sensors.

Figure 3I:
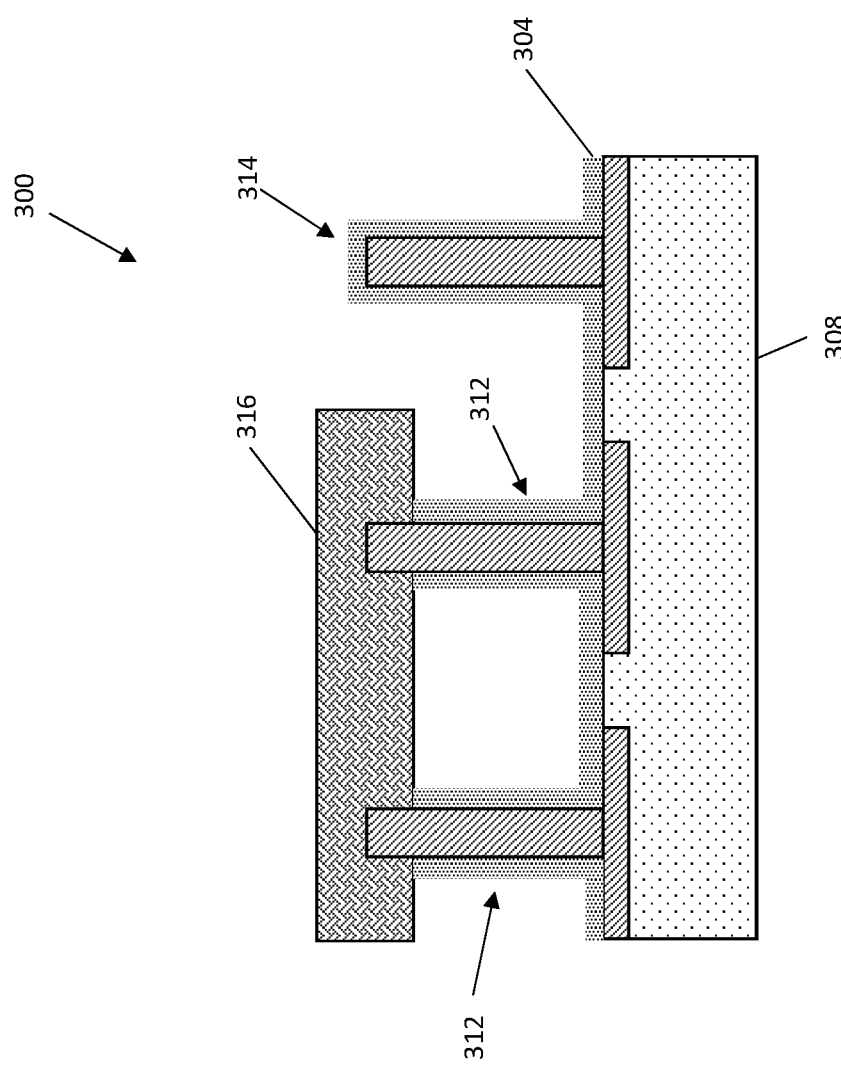

To form a resistivity sensor, a memory material 316 can be electro-polymerized on the partially exposed electrodes 312, as is shown in FIG. 3I. In some embodiments of the invention, voltage is selectively applied to adjacent partially exposed electrodes 312 and the partially exposed electrodes 312 are exposed to a conductive porous polymer precursor containing a desired template molecule (analyte), such as dopamine. Polymer can grow on exposed electrodes with applied voltage. In some embodiments of the invention, multiple locations of a structure 300 include pairs of adjacent partially exposed electrodes 312. In some embodiments of the invention, polymerization voltages can be separately applied to different pairs partially exposed electrodes 312 in the presence of different desired template molecules. Thus, different locations of a chip can be fabricated to be selective for different analytes.

Figure 3J:
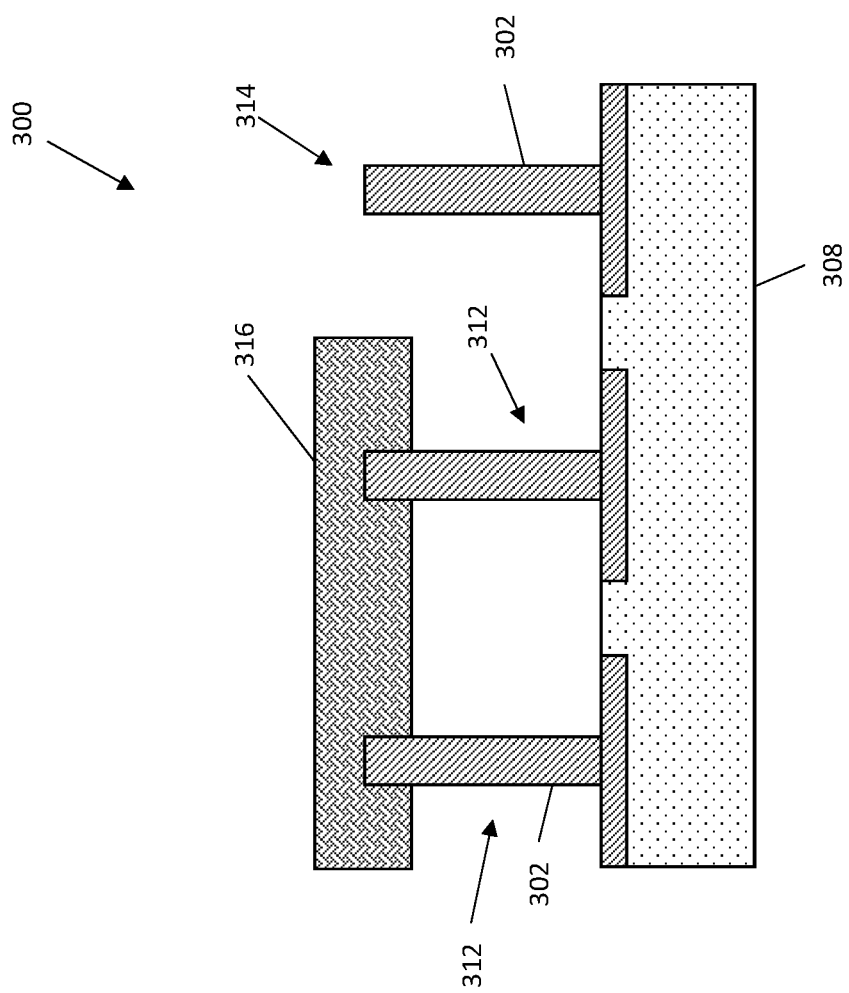

In some embodiments of the invention, the insulating layer 304 can be removed from the structure, for instance by stripping with DHF. FIG. 3J depicts an exemplary structure 300 after removal of the insulating layer 304.

Figure 3K:
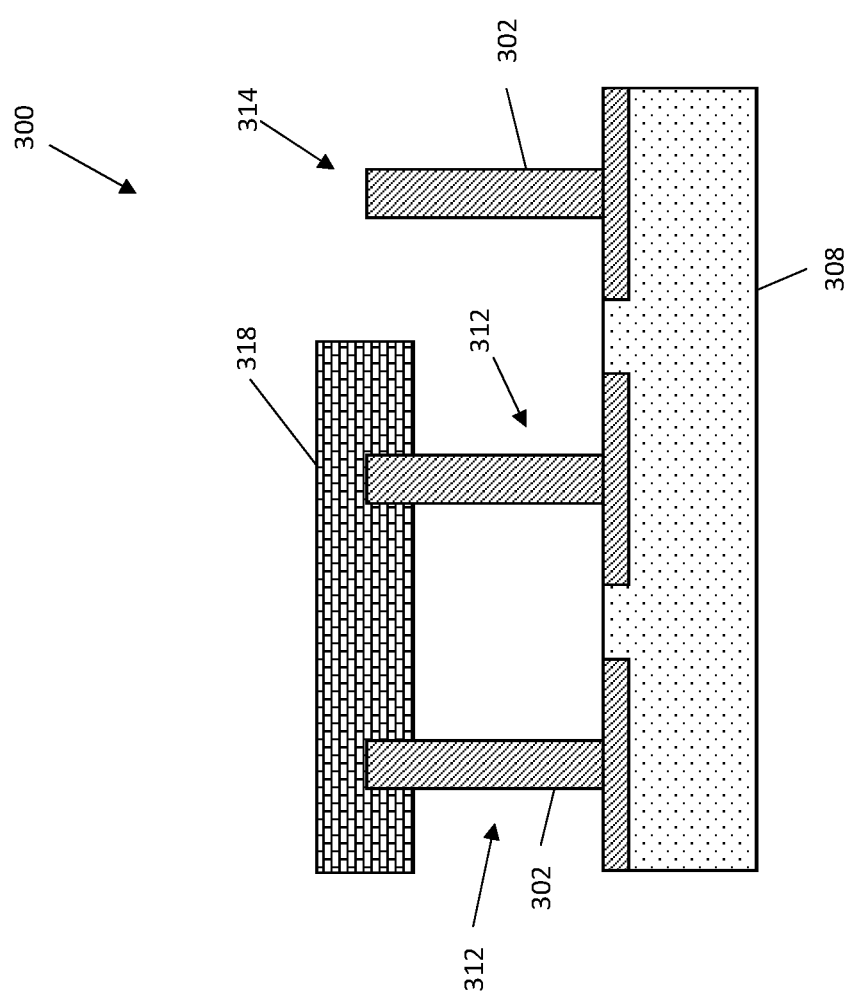

After forming a memory material 316 on the structure 300, the template molecules can be removed to generate an imprinted polymer 318, for instance by washing the memory material or by cycling the voltage of associated electrodes to dislodge the template molecules from the conductive porous polymer. FIG. 3K depicts an exemplary structure 300 including an imprinted polymer 318 and associated electrodes 312. The resultant imprinted polymer 318 will have a plurality of cavities, each having a size, shape, and binding affinity (e.g., through hydrophobic interactions and the like) specific to the template molecule, which can be the desired analyte.

Figure 3L:
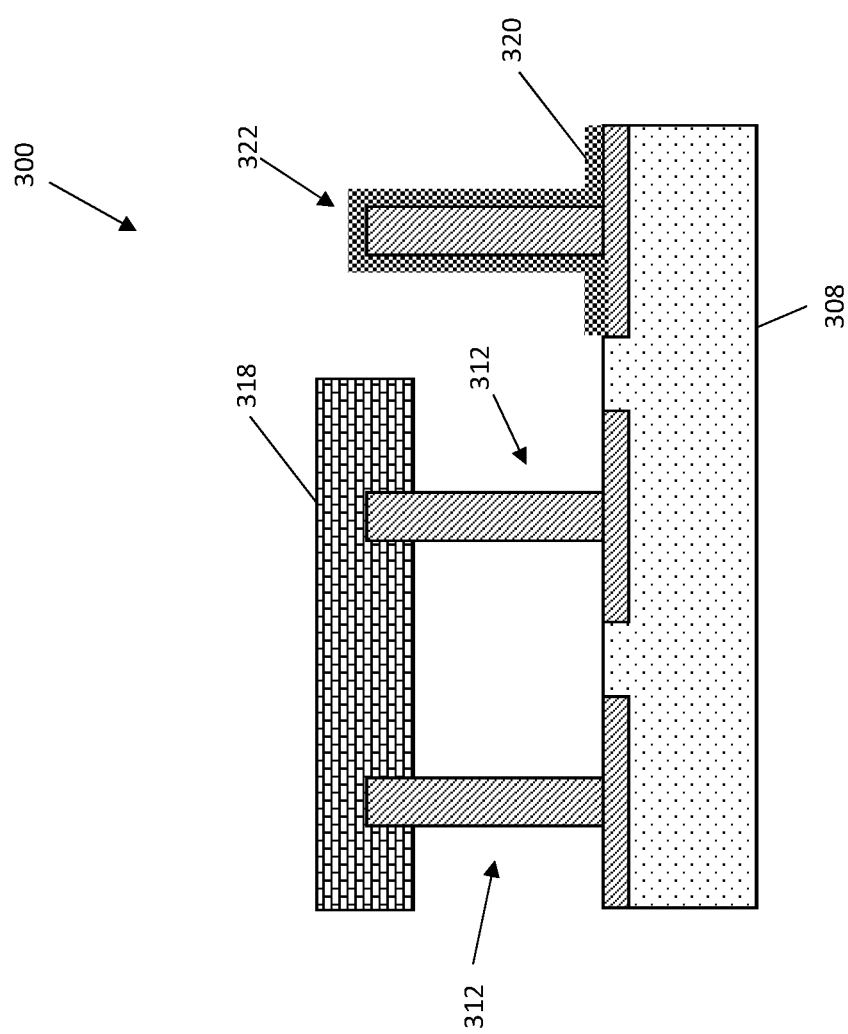

In some embodiments of the invention, one or more electrodes can be functionalized along the length of the nanopillar, with differing analyte sensitivity. In some embodiments of the invention, exposed electrodes not associated with imprinted polymer 322 can be associated with amperometric sensors. For example, in some embodiments of the invention, a voltage can be selectively applied to one or more nanopillars and the nanopillars exposed to amperometric sensor polymer 320. Amperometric sensor polymer 320 can include conductive polymer embedded with an enzyme selective for the desired analyte, such as glutamate oxidase. FIG. 3L depicts an exemplary structure 300 after formation of an amperometric sensor polymer 320 on a nanopillar. The amperometric sensor polymer 320 can be electropolymerized with both the enzyme and its substrate (the desired analyte). After polymerization, the substrate can be released from the polymer by washing or by applying voltage to the nanopillar sufficient to release the substrate, leaving an amperometric sensor polymer including a plurality of enzymatic binding sites with affinity to the desired analyte.

Exemplary conductive porous polymers that can be used to generate the imprinted polymer 318 and amperometric sensor polymer 320 can include, for instance, polyaniline with or without miscibility additives, polypyrrole, or poly (3,4-ethylenedioxythiophene) (PEDOT). Suitable miscibility additives can include, for example, phytic acid, silicon nanoparticles, silicon oxide nanoparticles, carbon nanoparticles, protobacteria proteins, including proteins from the genus *Geobacter*, and the like.

Figure 4:
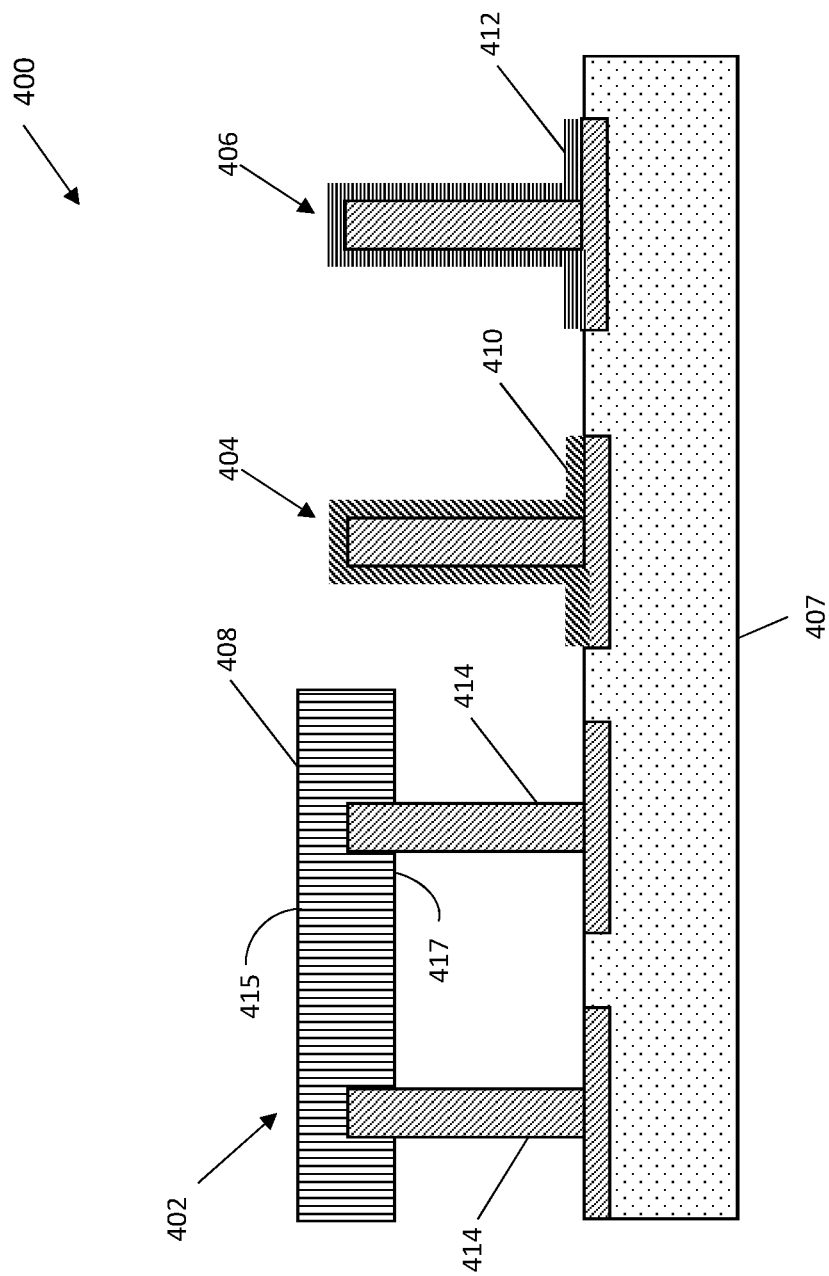
FIG. 4 depicts an exemplary biosensor according to embodiments of the invention.

FIG. 4 depicts an exemplary biosensor according to embodiments of the invention. As is shown in FIG. 4, a structure 400 can include both one or more resistivity sensors 402 and a plurality of amperometric sensors 404, and 406. The structure can be selective for a plurality of analytes, for instance by including an imprinted polymer 408 selective for a first analyte, such as dopamine, a first amperometric sensor 404 including a polymer embedded with a first enzyme 410 and a second amperometric sensor 406 including a polymer embedded with a second enzyme 412. The exemplary structure 400 includes a substrate 407, such as a silicon substrate. The imprinted polymer 408 can be formed at an upper portion of the associated nanopillars 414 providing accessible surfaces on a top portion 415 and a bottom portion 417 of the imprinted polymer. Providing an accessible bottom portion 417 of the imprinted polymer 408 can, for example, provide greater access and surface area to detect analyte and, thereby, could provide greater sensitivity in measurement relative, for example, to an imprinted polymer not including an accessible bottom portion 417.

Figure 5:
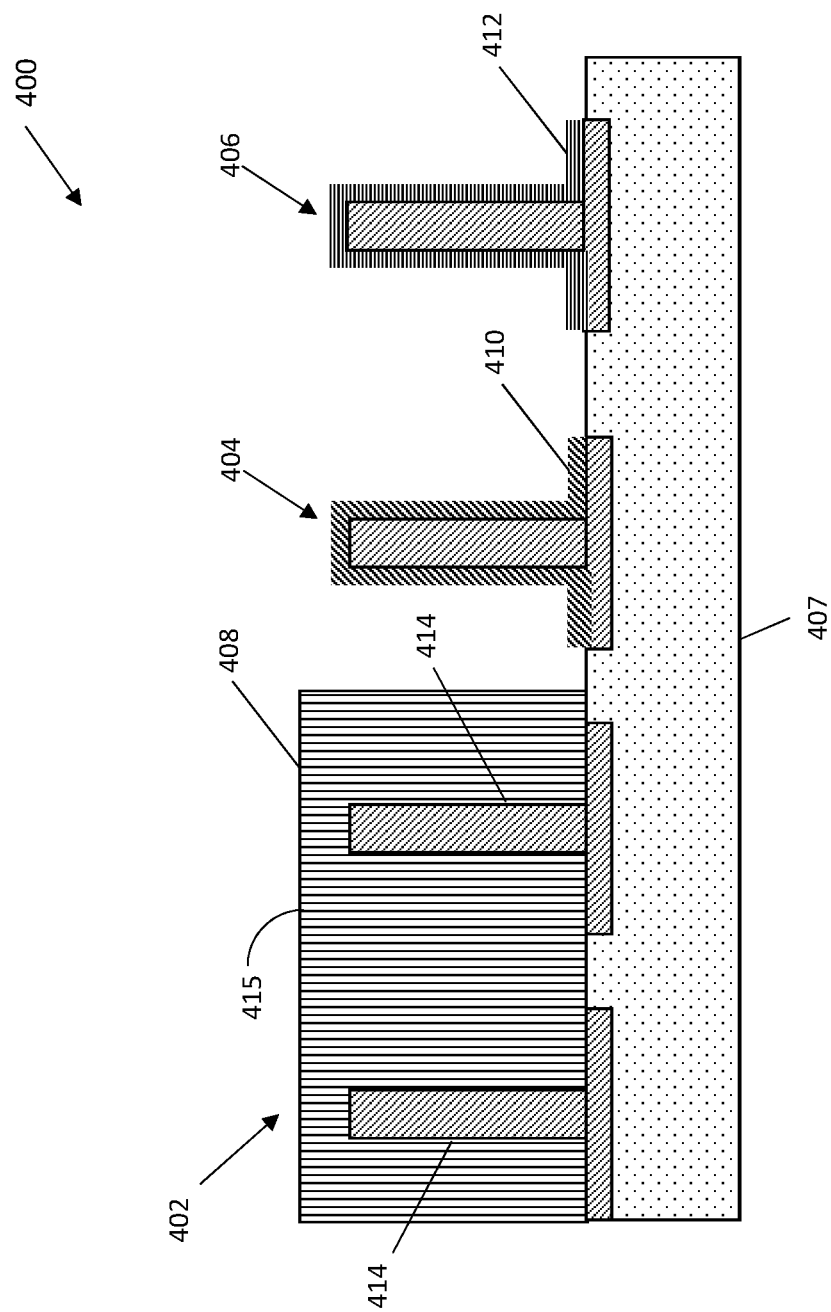
FIG. 5 depicts another exemplary biosensor according to embodiments of the invention.

FIG. 5 depicts another exemplary biosensor according to embodiments of the invention. As is shown in FIG. 5, a structure 400 can include both one or more resistivity sensors 402 and a plurality of amperometric sensors 404, and 406. The structure can be selective for a plurality of analytes, for instance by including an imprinted polymer 408 selective for a first analyte, such as dopamine, a first amperometric sensor 404 including a polymer embedded with a first enzyme 410 and a second amperometric sensor 406 including a polymer embedded with a second enzyme 412. The exemplary structure 400 includes a substrate 407, such as a silicon substrate. As is shown in FIG. 5, a resistivity sensor 408 can extend the length of and encompass the associated nanopillars 414. In this embodiment of the invention, the imprinted polymer 408 includes an accessible top portion 415.

Figure 6:
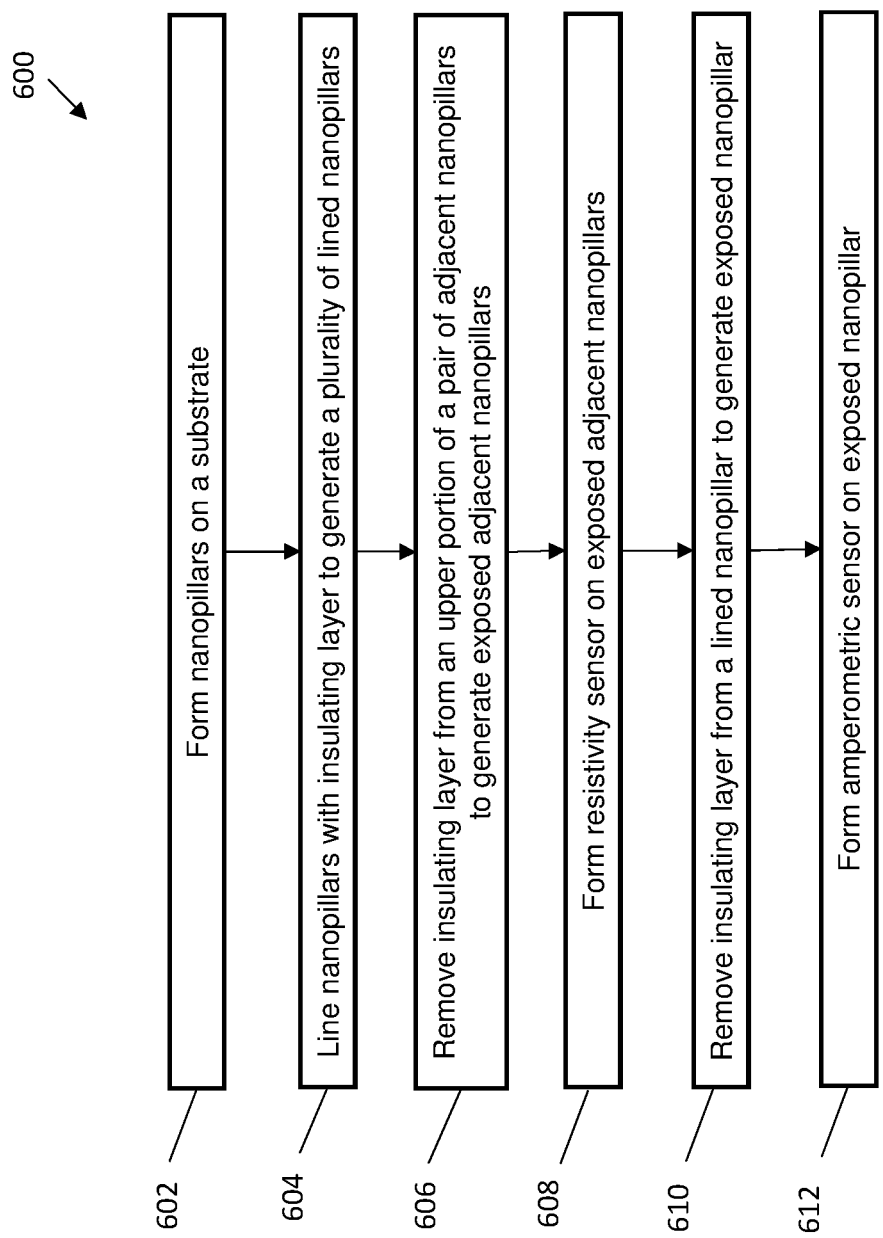
FIG. 6 depicts a flow diagram illustrating a method according to one or more embodiments of the invention.

FIG. 6 depicts a flow diagram illustrating an exemplary method 600 according to one or more embodiments of the invention. The method 600 includes, as shown at block 602, forming nanopillars on a substrate. The method 600 also includes, as shown at block 604, lining the nanopillars with an insulating layer to generate a plurality of lined nanopillars. The method 600 also includes, as shown at block 606, removing the insulating layer from an upper portion of a pair of adjacent nanopillars to generate exposed adjacent nanopillars. The method 600 also includes, as shown at block 608, forming a resistivity sensor on the exposed adjacent nanopillars. The method 600 also includes, as shown at block 610, removing the insulating layer from a lined nanopillar to generate an exposed nanopillar. The method 600 also includes, as shown at block 612, forming an amperometric sensor on the exposed nanopillar.

Figure 7:
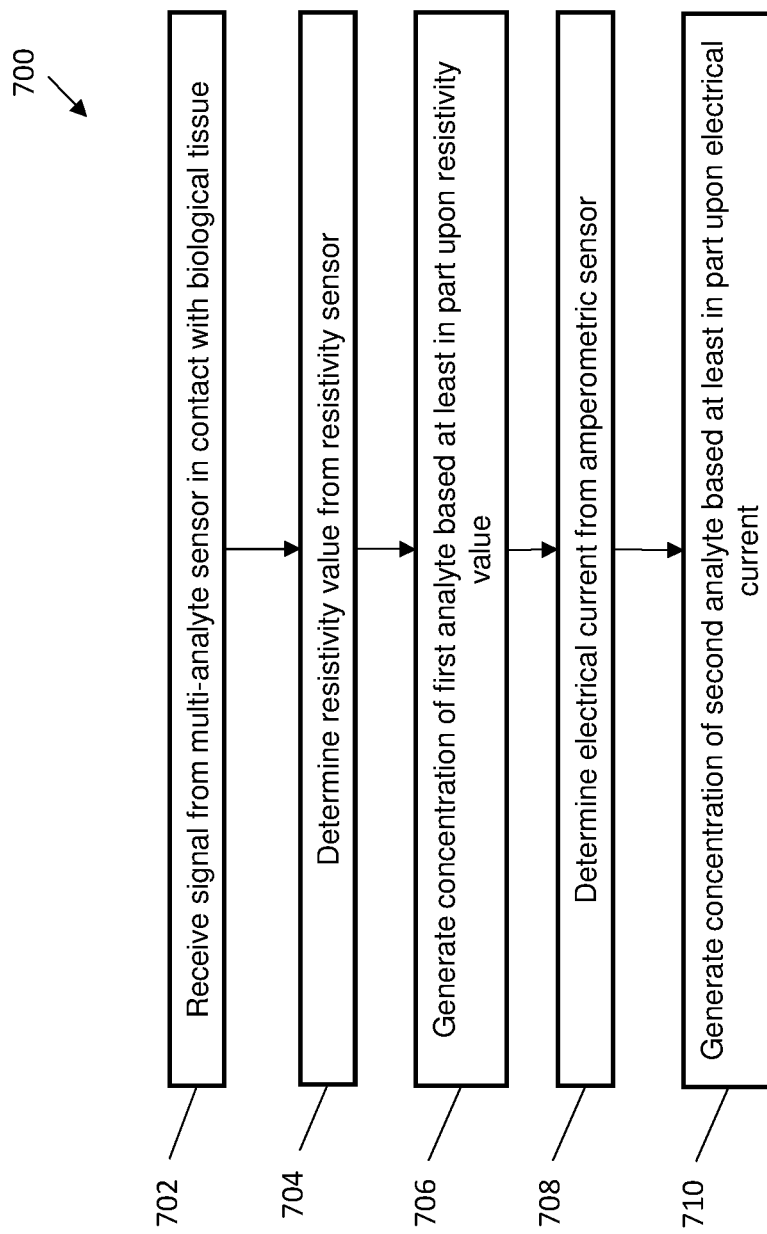
FIG. 7 depicts a flow diagram illustrating a method according to one or more embodiments of the invention.

FIG. 7 depicts a flow diagram illustrating an exemplary method 700 according to one or more embodiments of the invention. The method 700 includes, as shown at block 702, receiving a signal from a multi-analyte sensor in contact with a biological tissue. Biological tissue can include tissue containing one or more analytes under investigation and can include, for instance, neuronal tissue and/or brain tissue. The method 700 also includes, as shown at block 704, determining a resistivity value from a resistivity sensor. The resistivity value, for example, can be proportional to the concentration of an analyte. The method 700 also includes, as shown at block 706, generating a concentration of a first analyte based at least in part upon the resistivity value. The method also includes determining an electrical current from an amperometric sensor, as shown at block 708. The electrical current, for example, can be proportional to the concentration of an enzyme-active analyte. The method 700 also includes, as shown at block 710, generating a concentration of a second analyte based at least in part upon the electrical current.

Figure 8:
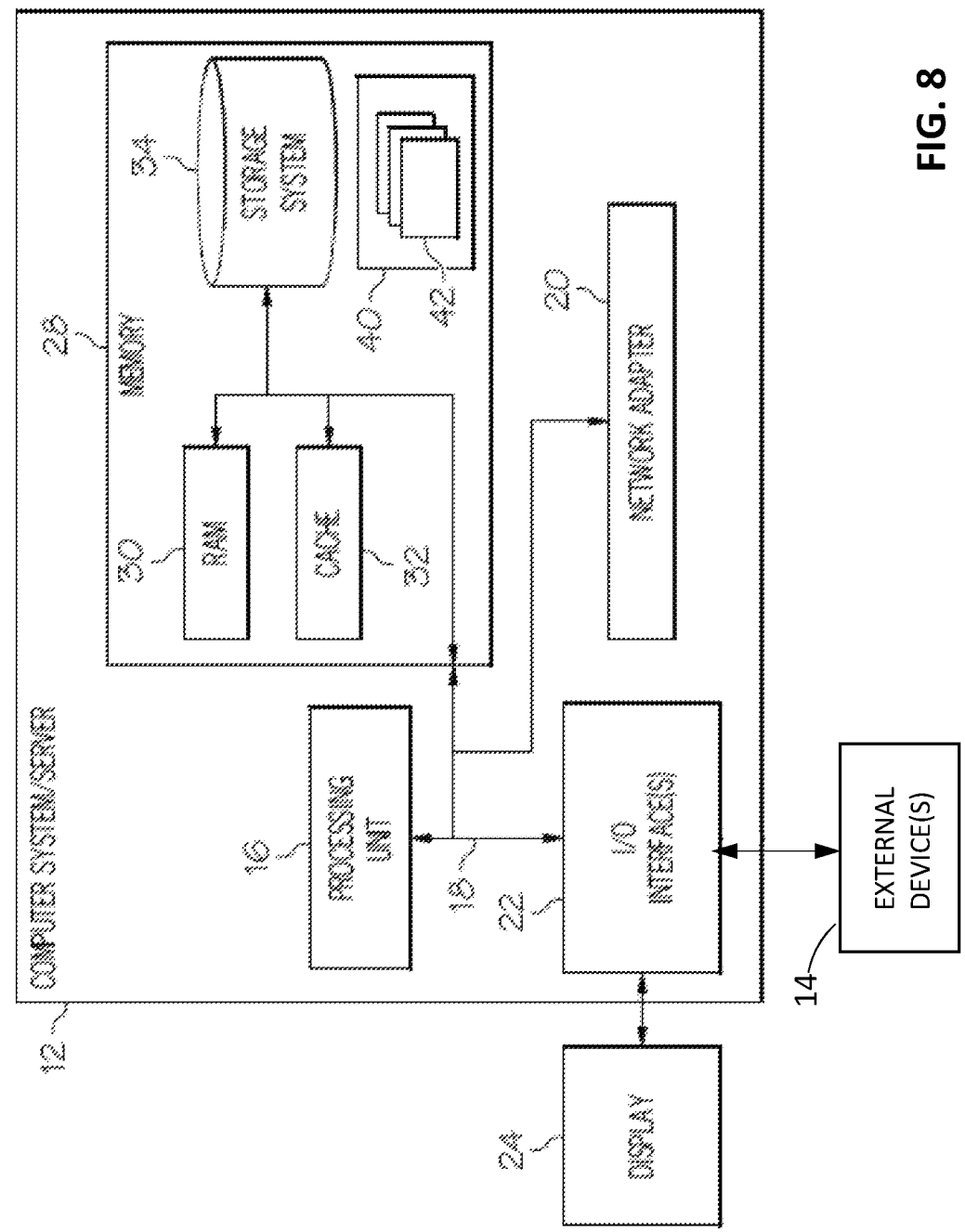
FIG. 8 depicts a computer system according to one or more embodiments of the invention.

Referring now to FIG. 8, a schematic of a computer system 800 is shown according to a non-limiting embodiment. The cloud computer system 800 is only one example of a suitable computer system and is not intended to suggest any limitation as to the scope of use or functionality of embodiments of the invention described herein. Regardless, computer system 800 is capable of being implemented and/or performing any of the functionality set forth hereinabove.

Computer system 800 includes a computer system/server 12, which is operational with numerous other general purpose or special purpose computing system environments or configurations. Examples of well-known computing systems, environments, and/or configurations that can be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 can be described in the general context of computer system-executable instructions, such as program modules, being executed by a computer system. Generally, program modules can include routines, programs, objects, components, logic, data structures, and so on that perform particular tasks or implement particular abstract data types. Computer system/server 12 can be practiced in distributed cloud computing environments where tasks are performed by remote processing devices that are linked through a communications network. In a distributed cloud computing environment, program modules can be located in both local and remote computer system storage media including memory storage devices.

As shown in FIG. 8, computer system/server 12 is shown in the form of a general-purpose computing device. The components of computer system/server 12 can include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 can include at least one program product having a set (e.g., at least one) of program modules that are configured to carry out the functions of embodiments of the invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out the functions and/or methodologies of embodiments of the invention as described herein.

Computer system/server 12 can also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Various embodiments of the present invention are described herein with reference to the related drawings.

Alternative embodiments can be devised without departing from the scope of this invention. Although various connections and positional relationships (e.g., over, below, adjacent, etc.) are set forth between elements in the following description and in the drawings, persons skilled in the art will recognize that many of the positional relationships described herein are orientation-independent when the described functionality is maintained even though the orientation is changed. These connections and/or positional relationships, unless specified otherwise, can be direct or indirect, and the present invention is not intended to be limiting in this respect. Accordingly, a coupling of entities can refer to either a direct or an indirect coupling, and a positional relationship between entities can be a direct or indirect positional relationship. As an example of an indirect positional relationship, references in the present description to forming layer "A" over layer "B" include situations in which one or more intermediate layers (e.g., layer "C") is between layer "A" and layer "B" as long as the relevant characteristics and functionalities of layer "A" and layer "B" are not substantially changed by the intermediate layer(s).

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

Additionally, the term "exemplary" is used herein to mean "serving as an example, instance or illustration." Any embodiment or design described herein as "exemplary" is not necessarily to be construed as preferred or advantageous over other embodiments or designs. The terms "at least one" and "one or more" are understood to include any integer number greater than or equal to one, i.e. one, two, three, four, etc. The terms "a plurality" are understood to include any integer number greater than or equal to two, i.e. two, three, four, five, etc. The term "connection" can include an indirect "connection" and a direct "connection."

References in the specification to "one embodiment," "an embodiment," "an example embodiment," etc., indicate that the embodiment described can include a particular feature, structure, or characteristic, but every embodiment may or may not include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

For purposes of the description hereinafter, the terms "upper," "lower," "right," "left," "vertical," "horizontal," "top," "bottom," and derivatives thereof shall relate to the described structures and methods, as oriented in the drawing figures. The terms "overlying," "atop," "on top," "positioned on" or "positioned atop" mean that a first element, such as a first structure, is present on a second element, such as a second structure, wherein intervening elements such as an interface structure can be present between the first element and the second element. The term "direct contact" means that a first element, such as a first structure, and a second element, such as a second structure, are connected without any intermediary conducting, insulating or semiconductor layers at the interface of the two elements.

The phrase "selective to," such as, for example, "a first element selective to a second element," means that the first element can be etched and the second element can act as an etch stop.

The terms "about," "substantially," "approximately," and variations thereof, are intended to include the degree of error associated with measurement of the particular quantity based upon the equipment available at the time of filing the application. For example, "about" can include a range of ±8% or 5%, or 2% of a given value.

As previously noted herein, for the sake of brevity, conventional techniques related to semiconductor device and integrated circuit (IC) fabrication may or may not be described in detail herein. By way of background, however, a more general description of the semiconductor device fabrication processes that can be utilized in implementing one or more embodiments of the present invention will now be provided. Although specific fabrication operations used in implementing one or more embodiments of the present invention can be individually known, the described combination of operations and/or resulting structures of the present invention are unique. Thus, the unique combination of the operations described in connection with the fabrication of a semiconductor device according to the present invention utilize a variety of individually known physical and chemical processes performed on a semiconductor (e.g., silicon) substrate, some of which are described in the immediately following paragraphs.

In general, the various processes used to form a microchip that will be packaged into an IC fall into four general categories, namely, film deposition, removal/etching, semiconductor doping and patterning/lithography. Deposition is any process that grows, coats, or otherwise transfers a material onto the wafer. Available technologies include physical vapor deposition (PVD), chemical vapor deposition (CVD), electrochemical deposition (ECD), molecular beam epitaxy (MBE) and more recently, atomic layer deposition (ALD) among others. Removal/etching is any process that removes material from the wafer. Examples include etch processes (either wet or dry), and chemical-mechanical planarization (CMP), and the like. Semiconductor doping is the modification of electrical properties by doping, for example, transistor sources and drains, generally by diffusion and/or by ion implantation. These doping processes are followed by furnace annealing or by rapid thermal annealing (RTA). Annealing serves to activate the implanted dopants. Films of both conductors (e.g., poly-silicon, aluminum, copper, etc.) and insulators (e.g., various forms of silicon dioxide, silicon nitride, etc.) are used to connect and isolate transistors and their components. Selective doping of various regions of the semiconductor substrate allows the conductivity of the substrate to be changed with the application of voltage. By creating structures of these various components, millions of transistors can be built and wired together to form the complex circuitry of a modern microelectronic device. Semiconductor lithography is the formation of three-dimensional relief images or patterns on the semiconductor substrate for subsequent transfer of the pattern to the substrate. In semiconductor lithography, the patterns are formed by a light sensitive polymer called a photo-resist. To build the complex structures that make up a transistor and the many wires that connect the millions of transistors of a circuit, lithography and etch pattern transfer steps are repeated multiple times. Each pattern being printed on the wafer is aligned to the previously formed patterns and slowly the conductors, insulators and selectively doped regions are built up to form the final device.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may include copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instruction by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein includes an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate possible implementations of fabrication and/or operation methods according to various embodiments of the present invention. Various functions/operations of the method are represented in the flow diagram by blocks. In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A method of fabricating a semiconductor device, the method comprising:
    forming a plurality of nanopillars on a substrate, the plurality of nanopillars comprising a first nanopillar and a pair of adjacent nanopillars;
    forming an insulating layer on the plurality of nanopillars to generate a plurality of lined nanopillars;
    depositing an organic planarization layer on the lined nanopillars;
    forming a hardmask layer over the first nanopillar, the hardmask layer open over the pair of adjacent nanopillars, wherein the hardmask layer is patterned on the organic planarization layer to generate a masked region and an unmasked region;
    etching the organic planarization layer in the unmasked region to expose a portion of the insulating layer on a subset of the plurality of lined nanopillars;
    removing the exposed portion of the insulating layer from upper portions of the pair of adjacent nanopillars to generate exposed adjacent nanopillar portions;
    removing the hardmask layer;
    forming a resistivity sensor on the exposed adjacent nanopillar portions;
    removing the insulating layer from the first nanopillar to generate an exposed first nanopillar portion; and
    forming an amperometric sensor on the exposed first nanopillar portion.

2. The method of claim 1, wherein forming the resistivity sensor comprises:
    selectively applying a voltage to the exposed adjacent nanopillar portions;
    contacting the exposed adjacent nanopillar portions with an analyte mixture comprising a conductive porous polymer precursor and a template molecule;
    electropolymerizing the analyte mixture to generate a conductive porous polymer comprising the template molecule, wherein the conductive porous polymer is in contact with the exposed adjacent nanopillar portions; and
    removing the template molecule from the conductive porous polymer to generate the resistivity sensor.

3. The method of claim 2, wherein the template molecule is dopamine.

4. The method of claim 1, wherein forming the amperometric sensor comprises
    selectively applying a voltage to the exposed first nanopillar portion;
    contacting the exposed first nanopillar portion with an enzyme mixture comprising a conductive porous polymer precursor, an enzyme, and a substrate, wherein the substrate is bound to the enzyme at an enzyme binding site;
    electropolymerizing the enzyme mixture to generate a conductive porous polymer comprising the enzyme and the substrate, wherein the conductive porous polymer lines the exposed nanopillar; and
    removing the substrate from the conductive porous polymer to generate the amperometric sensor.

5. The method of claim 4, wherein the substrate is selected from the group consisting of glutamate, lactate, glucose, choline, adenosine, and gamma-amino-butyric acid (GABA).

6. The method of claim 1, wherein forming the plurality of nanopillars on the substrate comprises:
    forming a resist layer on the substrate;
    patterning holes in the resist layer;
    plating a metal in the holes of the resist layer to form the nanopillars; and
    removing the resist layer from the substrate.

7. The method of claim 1, wherein the insulating layer comprises an oxide.

8. The method of claim 1, wherein generating the plurality of lined nanopillars comprises performing atomic layer deposition.

9. The method of claim 1, wherein the exposed nanopillar portions are the exposed adjacent nanopillar portions.

10. The method of claim 1, further comprising removing the organic planarization layer by plasma etching.

* * * * *